(12) United States Patent
Rault et al.

(10) Patent No.: US 7,972,625 B2
(45) Date of Patent: Jul. 5, 2011

(54) COATED DICLOFENAC TABLETS

(75) Inventors: Isabelle Rault, Segny (FR); Giovanna Marzano, Prangins (CH)

(73) Assignee: Novartis AG, Basel (CH)

( * ) Notice: Subject to any disclaimer, the term of this patent is extended or adjusted under 35 U.S.C. 154(b) by 297 days.

(21) Appl. No.: 10/572,687

(22) PCT Filed: Sep. 23, 2004

(86) PCT No.: PCT/EP2004/010696
§ 371 (c)(1), (2), (4) Date: Aug. 7, 2006

(87) PCT Pub. No.: WO2005/027879
PCT Pub. Date: Mar. 31, 2005

(65) Prior Publication Data
US 2007/0128277 A1 Jun. 7, 2007

(30) Foreign Application Priority Data

Sep. 24, 2003 (GB) .................................. 0322371.6
Nov. 3, 2003 (GB) .................................. 0325604.7

(51) Int. Cl.
*A61K 9/36* (2006.01)

(52) U.S. Cl. ........................................ 424/480; 424/472
(58) Field of Classification Search .................... None
See application file for complete search history.

(56) References Cited

U.S. PATENT DOCUMENTS

| 4,341,563 | A | * | 7/1982 | Kurihara et al. | ........... 106/174.1 |
| 4,690,927 | A | * | 9/1987 | Voss et al. | ...................... 514/282 |
| 5,009,897 | A | * | 4/1991 | Brinker et al. | |
| 6,013,823 | A | * | 1/2000 | Mamarella et al. | ........... 556/443 |
| 6,083,531 | A | * | 7/2000 | Humbert-Droz et al. | ..... 424/464 |
| 6,558,701 | B2 | * | 5/2003 | Bartholomaeus et al. | ..... 424/472 |
| 2006/0051420 | A1 | * | 3/2006 | De Haan et al. | .............. 424/472 |

FOREIGN PATENT DOCUMENTS

| EP | 0599767 | | 6/1994 |
| GB | 1594102 | * | 7/1981 |
| WO | WO 99/51209 A1 | * | 10/1999 |

OTHER PUBLICATIONS

SEPIFILM® LP product page, accessed Apr. 20, 2009.*

* cited by examiner

*Primary Examiner* — Michael G Hartley
*Assistant Examiner* — Nissa Westerberg
(74) *Attorney, Agent, or Firm* — Diane E. Furman; Gabriel Lopez

(57) ABSTRACT

The invention relates to coated tablets comprising the pharmaceutically active substance diclofenac. Said tablets further comprise a single film coating.

8 Claims, No Drawings

COATED DICLOFENAC TABLETS

The present invention concerns coated tablets comprising the pharmaceutically active substance diclofenac, which tablets are characterized by a special, very beneficial coating.

Diclofenac is a widely used non-steroidal anti-inflammatory drug (NSAID), and in the context of this document the term "diclofenac" is to be understood as including diclofenac (free acid) and pharmaceutically acceptable salts thereof, e.g. diclofenac sodium, diclofenac potassium or diclofenac epolamine. In particular preferred is diclofenac K.

Diclofenac tablets with coatings are known in the art. The general purpose of a said coating is to protect the tablet core, including the active substance, mainly against moisture, oxygen and light, and so to increase the stability, i.e. the shelf life, of the tablet. The coating is also used to ease the swallowing of the tablet.

A polymer that is particularly well suited to form the basis of a film coating for diclofenac tablets is hydroxypropyl methylcellulose (HPMC). It is ideal in providing a film forming effect, it also provides an effective moisture barrier, and in general reduces permeability for gases. A corresponding film coated tablet comprising 12.5 mg diclofenac K is known in the art. Said film coated tablet is manufactured by first coating the tablet core with a white coating premix consisting of HPMC, polyethylene glycol 400, polysorbate 80 and titanium dioxide (as whitening dyestuff). The coated tablet core so obtained is then subjected to a second coating step with a clear coating premix consisting of HPMC, polyethylene glycol 400 and maltodextrin. Said second coating is necessary for polishing the tablets and so give them a neat appearance.

The downsides of said film coated diclofenac K tablet are as follows. As two coating steps have to be performed, the coating process is in general rather difficult to perform. In addition, the tablet is in the form of a so-called caplet which shape is in general known to be more difficult to coat. This means, the coating process is lengthy and requires strict quality control to avoid, or separate out, film coated tablets having ridges or picking on their surface. Moreover, the taste of said twice coated tablet is not very pleasant due to the specific coating compositions used.

It is therefore a goal of the present invention to avoid said disadvantages and provide a diclofenac tablet with a film coating based on HPMC, which tablet can be manufactured by a simpler process, within a shorter process time, and which tablet is essentially tasteless.

Thus, the present invention concerns a film coated tablet comprising
(a) a tablet core comprising diclofenac or a pharmaceutically acceptable salt thereof, and
(b) a coating comprising HPMC, stearic acid and microcrystalline cellulose.

In the field of pharmaceutical technology, a "coating", e.g. coating (b), is completely covering the surface of the tablet core (a), that is to say the coating (b) is completely enrobing the tablet core (a).

Preferably, the film coated tablet has one single coating (b).

More preferably, the film coated tablet consists essentially of (a) and (b) as defined hereinabove or hereinbelow. With respect to the tablet cores (a) this means, that, preferably, diclofenac or a pharmaceutically acceptable salt thereof, is the only pharmaceutically active substance present.

Preferably, the coating (b) in addition comprises titanium dioxide as whitening dyestuff.

In the tablet core (a), diclofenac is typically present in an amount of 10-100 mg, preferably 10-50 mg. The coating of the present invention is particularly useful for enrobing tablet cores comprising diclofenac K. In particular, 12.5 mg of diclofenac K are used.

Preferably, the tablet core (a) comprises microcrystalline cellulose. By including microcrystalline cellulose into the composition of both the tablet core (a) and the coating (b), the compatibility between the core and the coating layer is enhanced. Typically, microcrystalline cellulose is present in an amount of 2-15%, preferably 5-10%, (w/w) of the tablet core composition.

In general, tablet cores (a) are composed of components well known in the art and are manufactured in a manner known per se.

EXAMPLE 1

Film Coated Tablet Comprising 12.5 ma Didofenac K

| Core composition | |
|---|---|
| diclofenac K | 12.5 mg |
| magnesium stearate | 2.025 mg |
| povidone | 4.05 mg |
| colloidal anhydrous silica | 8.025 mg |
| microcrystalline cellulose | 13.5 mg |
| sodium starch glycolate | 26.7 mg |
| lactose monohydrate | 33.45 mg |
| maize starch | 99.75 mg |

Coating Composition

A mixture of 60-70% HPMC, 8-12% stearic acid, 5-15% microcrystalline cellulose and 10-20% titanium dioxide (e.g. "Sepifilm LP 770 White", company Seppic) for a total mass of 6.0 mg per tablet is used.

Tablet cores are manufactured in a manner known per se, e.g. by granulation and tabletting of the finely powdered components of the core composition. The tablet cores are coated in a coater in a manner known per se.

COMPARATIVE EXAMPLE 1

Film Coated Tablet Comprising 12.5 mg Diclofenac K

| Core composition | |
|---|---|
| diclofenac K | 12.5 mg |
| magnesium stearate | 2.025 mg |
| povidone | 4.05 mg |
| silica colloidal anhydrous | 8.025 mg |
| microcrystalline cellulose | 13.5 mg |
| sodium starch glycolate | 26.7 mg |
| lactose monohydrate | 33.45 mg |
| maize starch | 99.75 mg |

Coating Composition 1

A mixture of ca. 60% HPMC, ca. 8% Macrogol 400 (=Polyethylene glycol.400), ca. 1% Polysorbate 80 [=polyoxyethylene (20) sorbitan monooleate] and ca. 31% titanium dioxide (e.g. Opadry® "White coating premix", company Colorcon) for a total mass of 8.0 mg per tablet is used.

Coating Composition 2

Mixture of ca. 63% HPMC, ca. 10% Macrogol 400 and ca. 27% maltodextrin (e.g. Opadry® "Clear coating premix", company Colorcon) for a total mass of 1.0 mg per tablet is used.

Tablet cores are manufactured in a manner known per se, e.g. by direct compression of the finely powdered. components of the core composition. The tablet cores are first coated with coating composition 1 in a coater. Then, the coated tablet cores are further coated with coating composition 2.

Comparison between Example 1 and Comparative Example 1

|  | Example 1 | Comparative Example 1 |
| --- | --- | --- |
| Number of coatings | 1 | 2 |
| Mass of coating (mg/tablet) | 6 | 9 |
| Process time | 60 min | 95 min |
| Process issues | none | need to separate out tablets with appearance failures (ridges, picking on tablet surface) |
| Taste of final product | tasteless | not pleasant |

The great advantages of Example 1, both with respect to a simpler and shorter process and with respect to the properties of the final product, are evident.

The invention claimed is:

1. A film coated tablet consisting essentially of
   (a) a tablet core comprising only one pharmaceutically active substance, which is diclofenac or a pharmaceutically acceptable salt thereof, and
   (b) a single film coating comprising 60-70% (w/w) hydroxypropyl methylcellulose, 8-12% (w/w) stearic acid, 5-15% (w/w) microcrystalline cellulose, and 10-20% (w/w) titanium dioxide based on the weight of the coating alone.

2. A film coated tablet of claim 1, wherein the tablet core comprises diclofenac potassium.

3. A film coated tablet of claim 2, wherein the diclofenac potassium is present in an amount of 10-50 mg.

4. A film coated tablet of claim 2, wherein the diclofenac potassium is present in an amount of 12.5 mg.

5. A film coated tablet of consisting essentially of
   (a) a tablet core comprising only one pharmaceutically active substance, which is diclofenac or a pharmaceutically acceptable salt thereof, and
   (b) a single film coating comprising 60-70% (w/w) hydroxypropyl methylcellulose, 8-12% (w/w) stearic acid, 5-15% (w/w) microcrystalline cellulose, and 10-20% (w/w) titanium dioxide based on the weight of the coating alone;
   wherein the tablet core comprises microcrystalline cellulose.

6. A film coated tablet of claim 5, wherein the microcrystalline cellulose is present in the tablet core in an amount of 2-15% (w/w) of the tablet core.

7. A film coated tablet of claim 6, wherein the microcrystalline cellulose is present in the tablet core in an amount of 5-10% (w/w) of the tablet core.

8. A film coated tablet which consists of:
   (a) a tablet core consisting essentially of:

| | |
| --- | --- |
| diclofenac K | 12.5 mg |
| magnesium stearate | 2.025 mg |
| povidone | 4.05 mg |
| silica colloidal anhydrous | 8.025 mg |
| microcrystalline cellulose | 13.5 mg |
| sodium starch glycolate | 26.7 mg |
| lactose monohydrate | 33.45 mg |
| maize starch | 99.75 mg; and |

(b) a single film coating comprising 60-70% (w/w) hydroxypropyl methylcellulose, 8-12% (w/w) stearic acid, 5-15% (w/w) microcrystalline cellulose, and 10-20% (w/w) titanium dioxide based on the weight of the coating.

* * * * *